(12) United States Patent
Lee et al.

(10) Patent No.: US 8,945,043 B2
(45) Date of Patent: Feb. 3, 2015

(54) MEDICAL DEVICE WITH CONTEXTUAL AWARENESS

(71) Applicant: Zyno Medical LLC., Natick, MA (US)

(72) Inventors: Chaoyoung Lee, Weston, MA (US); James Zhimin Yan, West Roxbury, MA (US); Mei Zhang, Sharon, MA (US)

(73) Assignee: Zyno Medical, LLC., Natick, ME (US)

( * ) Notice: Subject to any disclaimer, the term of this patent is extended or adjusted under 35 U.S.C. 154(b) by 142 days.

(21) Appl. No.: 13/687,728

(22) Filed: Nov. 28, 2012

(65) Prior Publication Data

US 2013/0144206 A1 Jun. 6, 2013

Related U.S. Application Data

(60) Provisional application No. 61/565,662, filed on Dec. 1, 2011.

(51) Int. Cl.
*A61M 31/00* (2006.01)
*A61M 5/172* (2006.01)
*G06F 19/00* (2011.01)

(52) U.S. Cl.
CPC ......... *A61M 5/1723* (2013.01); *G06F 19/3468* (2013.01); *A61M 2205/3576* (2013.01); *A61M 2205/502* (2013.01); *G06F 19/326* (2013.01)
USPC ........................................... 604/66

(58) Field of Classification Search
USPC ............................... 604/65, 66, 67
See application file for complete search history.

(56) References Cited

U.S. PATENT DOCUMENTS

| | | |
|---|---|---|
| 5,643,212 A | 7/1997 | Coutre et al. |
| 6,519,569 B1 | 2/2003 | White et al. |
| 6,671,563 B1 | 12/2003 | Engelson et al. |
| 6,731,989 B2 | 5/2004 | Engleson et al. |
| 7,018,361 B2 | 3/2006 | Gillespie, Jr. et al. |
| 7,107,106 B2 | 9/2006 | Engleson et al. |
| 7,236,936 B2 | 6/2007 | White et al. |
| 7,645,258 B2 | 1/2010 | White et al. |
| 7,766,863 B2 | 8/2010 | Gillespie, Jr. et al. |
| 7,771,385 B2 | 8/2010 | Eggers et al. |
| 7,933,780 B2 | 4/2011 | De La Huerga |
| 7,976,508 B2 | 7/2011 | Hoag |
| 8,075,514 B2 | 12/2011 | Butterfield et al. |
| 8,172,798 B2 | 5/2012 | Hungerford et al. |
| 2003/0106553 A1 | 6/2003 | Vanderveen |
| 2006/0116639 A1 | 6/2006 | Russell |
| 2006/0200369 A1 | 9/2006 | Batch et al. |
| 2007/0251835 A1* | 11/2007 | Mehta et al. ................... 205/783 |
| 2007/0253021 A1* | 11/2007 | Mehta et al. ................... 358/1.15 |
| 2007/0254593 A1* | 11/2007 | Jollota et al. ............... 455/67.11 |
| 2007/0258395 A1* | 11/2007 | Jollota et al. ................... 370/310 |
| 2009/0203329 A1 | 8/2009 | White et al. |
| 2011/0196306 A1 | 8/2011 | De La Huerga |
| 2011/0264044 A1 | 10/2011 | Bartz |

* cited by examiner

*Primary Examiner* — Aarti B Berdichevsky
(74) *Attorney, Agent, or Firm* — Boyle Fredrickson, S.C.

(57) ABSTRACT

A medical device, such as an infusion pump, obtains a contextual awareness of its operation by communicating with centralized patient records and or other medical equipment communicating with a common patient, and/or provides real time advisory information, at care point or remotely. A protocol obtained by the medical device from a protocol server provides context-aware protocols and necessary predicate information for those protocols. This predicate information may be discovered by the medical device communicating with electronic medical records and the associated medical equipment.

16 Claims, 4 Drawing Sheets

MEDICAL DEVICE WITH CONTEXTUAL AWARENESS

CROSS REFERENCE TO RELATED APPLICATION

This application claims the benefit of U.S. provisional application 61/565,662 filed Dec. 1, 2011 and hereby incorporated by reference in its entirety.

BACKGROUND OF THE INVENTION

The present invention relates to medical devices that may monitor and manage patients and patient treatment, and in particular to such medical equipment having the capacity to provide patient-specific advisory information.

Medical devices, for example, including heart monitors, blood oxygen sensors, infusion pumps, and the like play an important role in providing real-time health support of patients in the hospital and clinical environment. Such equipment may operate automatically to monitor vital signs of the patient and to administer drugs and the like. Normally, a healthcare professional such as a nurse, following the advice of a physician, may input settings to a microprocessor or the like associated with such equipment defining the operation of the equipment. The nurse may then be free to attend to other duties, requiring only periodic monitoring of the equipment.

Such medical devices may provide certain alarm signals indicating problems that may relate to the patient or to the interaction between the patient and the machine including certain machine fault conditions. These alerts are based on rules internally programmed into the medical devices related to the particular function of the machine. For example, an infusion pump may report an occlusion in the IV line indicated by a pressure rise.

In addition, it is known to program drug delivery systems such as infusion systems, with facts about the drugs they deliver, for example, parameter limits for intravenous infusion for particular drugs. When such infusion systems are properly notified of the drug being delivered, they may provide for a check of their own delivery settings against those parameter limits providing alert if there is a conflict between the two.

With increasing availability of data sources for drug facts, disease treatment protocols, clinical therapy protocols, etc, together with advancements in developing "smart" medical devices with wireless communication and advisory features, better systems and methods of use can be developed to utilize available knowledge base for a specific patient with specific conditions. The advisory can be provided by a medical device (s) or other related devices. The advisory can be made on a remote site, or on site. The timing can be real time, in advance, or post-treatment. Such system(s) and method(s) are provided in this patent application.

SUMMARY OF THE INVENTION

The present invention provides a medical device that may provide advisory information, such as recommended operating parameters or checks for operating errors and/or alert conditions based on contextual knowledge about the particular patient being treated. Contextual awareness can be obtained by a sharing of information among medical devices monitoring or treating the patent (identified by a common patient identification number held by the medical equipment and interrogation of central medical records in the hospital or the like for patient-specific information important to the function performed by the medical equipment for a particular patient.

In one embodiment, the present invention provides a medical device providing an interventional element communicating with the patient to perform a medical procedure on the patient, a data input device for receiving data related to a interventional task in delivery of the liquid medicament, a data communication link for electronic data communication with external devices, and an electronic controller. The electronic controller may execute a stored program to: (a) transmit the data related to the interventional task to an external data serving device to receive an operation protocol related to the interventional task and an identification of required predicate data; (b) discover predicate data of the required predicate data from at least one external predicate data device; and (c) monitor execution of the interventional task according to the received operation protocol and predicate data from the at least one external data serving device and external predicate data device.

It is thus a feature of at least one embodiment of the invention to provide a medical device that can obtain effective contextual understanding of its task by guided sharing of information with other associated devices and data sources. Task data and in some cases patient identification information provide keys for data sharing identifying a common patient for sensor data and by identifying a context-aware protocol that establishes a framework for the necessary shared data.

The interventional element may be a pump for delivering a liquid medicament and the data related to interventional task may include drug information identifying the liquid medicament and delivery information identifying at least one of the delivery rate and volume for the liquid medicament.

It is thus a feature of at least one embodiment of the invention to make use of information normally entered into a medical pump as an index for context-aware protocol information about procedures.

The data related to the pump task may include patient identification information.

It is thus a feature of at least one embodiment of the invention to provide a mechanism for intercommunication of devices operating on a single patient and thus possibly having a common patient identification number.

The external predicate data device may be a hospital database providing clinical information about the patient based on the patient identification information.

It is thus a feature of at least one embodiment of the invention to obtain deeper knowledge about the patient such as is available in hospital records.

The external predicate data device may be a medical monitoring system proximate to the medical pump providing real-time medical data for the patient based on the patient identification information.

It is thus a feature of at least one embodiment of the invention to promote the sharing of information among multiple monitoring that can improve the delivery of health care to the patient.

The medical monitoring system may be for example, a blood pressure monitor, a blood oximeter, a glucose monitor; and a respiration monitor.

It is thus a feature of at least one embodiment of the invention to provide a system that can work with common bedside monitoring equipment to enhance the delivery of medicament by a pump system.

The data input device may be selected from the group consisting of: a keyboard, RFID tag reader, and a barcode scanner.

It is thus a feature of at least one embodiment of the invention to provide for automatic entry of pump task data for example from barcodes or other labels on the medicament.

The pump may be selected from the group consisting of an infusion pump and a syringe pump.

It is thus a feature of at least one embodiment of the invention to provide a system to enhance operation of common medical treatment devices.

The data communication link may be a wireless communication link.

It is thus a feature of at least one embodiment of the invention to promote mobility of the devices as may be necessary in a healthcare environment.

The medical pump may further include an alarm providing an alarm to a user of the medical pump and wherein the electronic controller further executes the stored program to activate the alarm according to the rules of the context-aware protocol.

It is thus a feature of at least one embodiment of the invention to operate a medical pump in an advisory role based on its enhanced contextual understanding.

It should be understood that the invention is not limited in its application to the details of construction and arrangements of the components set forth herein. The invention is capable of other embodiments and of being practiced or carried out in various ways. Variations and modifications of the foregoing are within the scope of the present invention. It also being understood that the invention disclosed and defined herein extends to all alternative combinations of two or more of the individual features mentioned or evident from the text and/or drawings. All of these different combinations constitute various alternative aspects of the present invention. The embodiments described herein explain the best modes known for practicing the invention and will enable others skilled in the art to utilize the invention.

DETAILED DESCRIPTION OF THE PREFERRED EMBODIMENT

Figure 1:
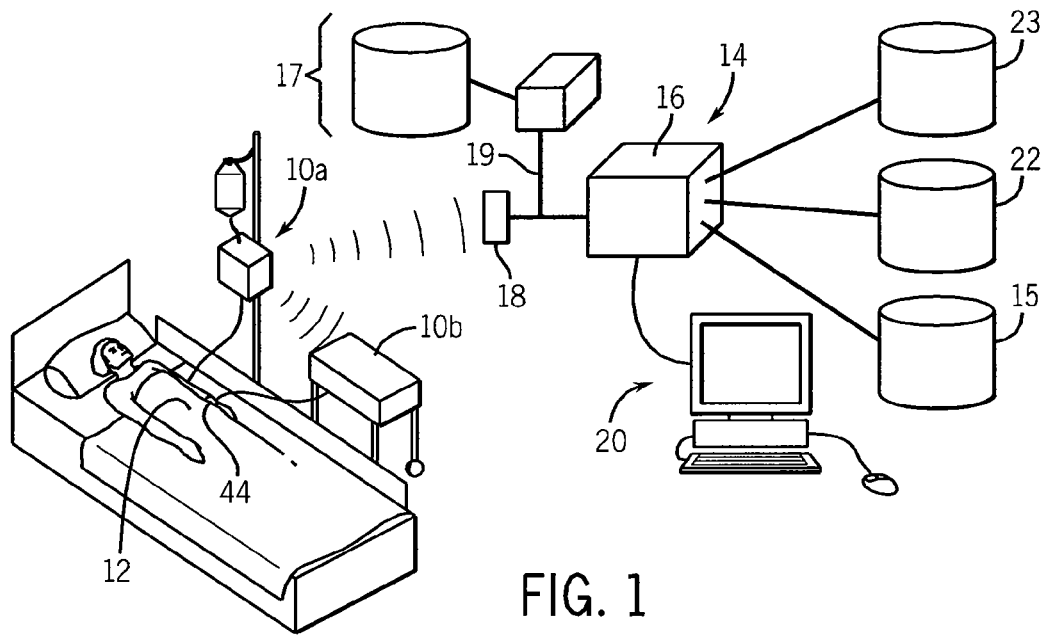
FIG. 1 is a simplified representation of the hospital environment showing an interventional medical device in the form of a medical pump intercommunication with a medical monitoring device suitable for use with the present invention, the medical pump further communicating with databases such as a central medical records system, and a protocol database.

Referring now to FIG. 1, medical devices 10a and 10b may be positioned adjacent to a patient 12 for providing healthcare monitoring and/or interventional services in a hospital or other environment. Medical device 10a, as depicted, may be an infusion pump for drug delivery and medical device 10b may be a general monitoring system, for example, monitoring heart rate, respiration, pulse, temperature, blood oxygen or the like. In this respect, medical devices 10 can both monitor the patient and effect patient treatments.

As will generally be understood in the following description, according to the present invention, a given medical device 10 may communicate both with other medical devices 10 attending to the same patient 12 and with databases such as a central medical record system 14 or an external context-aware protocol database 17 via the internet 19. This communication may be by a variety of means including electrical or optical cables or, as shown, wireless communication.

The central medical record system 14 may, for example, provide a central record server 16 communicating via wireless transceiver 18 with the medical devices 10 and by a standard network circuit or the like with multiple data terminals 20 that may be staffed by healthcare personnel who may enter or access patient medical records and read alerts and monitor operation of the medical devices 10 or the like. The central record server 16 may communicate with an electronic medical record database 22 holding patient medical records linked to patient identification numbers. As a general matter, medical record database 22 will link a patient identifier uniquely identifying a patient with various clinical information about the patient including: weight, height, gender, age, allergies and the like.

The central record server 16 may also communicate with a context-aware protocol database 15 for particular context-aware protocols or rules for treating a patient, and/or drug fact database 23 with information for specific drugs. In the case of treating the patient by the introduction of a liquid medicament, for example using a medical pump, the context-aware protocol database 15 may hold data indicating types of drugs and their preferred delivery rates in rate and total quantity as a function of particular static predicate data (such as patient gender or weight) and real-time predicate data such as blood pressure, glucose level and the like.

The external context-aware protocol database 17 will generally differ from the central record server 16 by the absence of clinical data about the patient but may provide a source of information similar to the context-aware protocol database 15 and the drug fact database 23.

An example context-aware protocol in the external protocol database 17 or the treatment protocol database 15, for a medical pump, may identify patient blood pressure as predicate data and provide a protocol that defines a range of blood pressure during which the pump may operate so as to cause termination of pump operation when blood pressure moves out of this range. A second example context-aware protocol for a medical pump may identify blood glucose as predicate data and provide a range of blood glucose during which the pump may operate and cause termination of pump operation when blood glucose moves out of this range.

Figure 2:
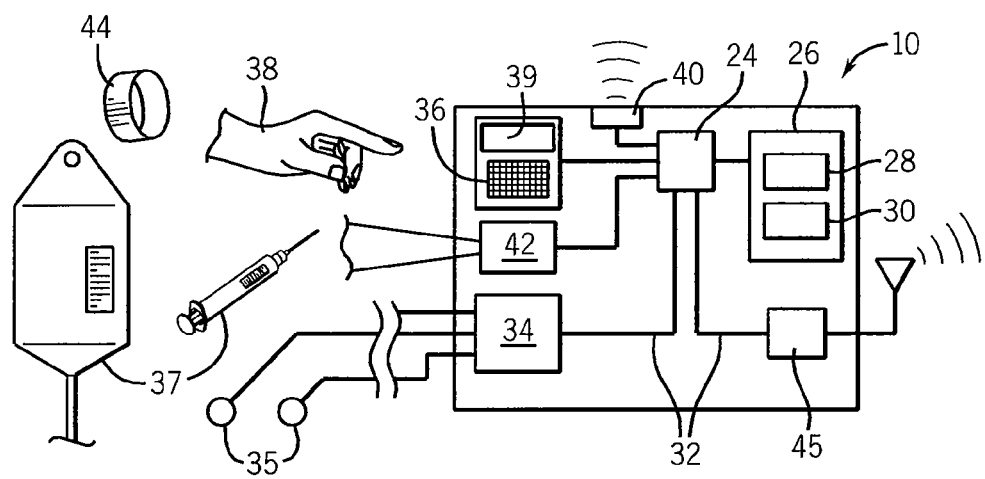
FIG. 2 is a block diagram of the principal hardware components of a medical device representative of the devices of FIG. 1, the medical device providing wireless communication and other inputs for obtaining pump task data, patient identification information and context-aware protocol and predicate data for implementing the pump task.

Referring now to FIG. 2, the medical devices 10 may generally include a processor 24 communicating with a memory 26 (possibly included on the same integrated circuit), the latter holding a program 28 providing an operating system for the medical device 10 and specific executable programs as will be described below. The memory 26 may also hold data structures 30 used by the program 28 as will be described below.

In the case of memory being external to the processor, the processor 24 may communicate with the memory 26 on a central bus or multiple I/O lines 32 which also allow the processor 24 to communicate with an interface 34 to various sensors and actuators 35 specific to the function of the particular medical devices 10. Such sensors 35 may include, for example, pressure sensors, temperature sensors, oxygen sensors, ultrasonic sensors and other specialized sensors well known in the art. Such actuators 35 may include, for example, motors, heaters, annunciators, and the like. Different medical devices 10 will generally have different subsets of sensing capability and intercommuncation will be necessary to obtain a context of the patient treatment.

The processor 24 may also communicates with a data entry keypad 36, for example a membrane switch array, allowing data to be entered by medical personnel 38 associated with a particular task to be executed by the medical device 10. The data entry keypad 36 may be associated with an output screen (such as an LCD alphanumeric display) for facilitating the data entry and review and for providing output to medical personnel 38. A more advanced touch screen may be used for inputting and displaying information. The data entry keypad 36, for example, may be used to enter patient identification information, drug information, and drug delivery rate or volume, in the case of a medical pump.

The processor 24 may further communicate with context sensors 40 and 42 which may provide important contextual information about the operation of the medical device 10. In one example, context sensor 40 may be an RFID tag reader for identifying drug products 37, for example, as held in an IV bag or syringe and marked as to drug type and treatment parameters by an RFID tag, as intended to be delivered by the medical device 10a. Context sensor 42, for example, may be a barcode reader, for example, for scanning a barcode wristband 44 on a patient 12 (shown in FIG. 1), or the IV bag or syringe or the like.

The processor 24 may also communicate with a wireless transceiver 45, for example, a ZigBee, Wi-Fi, Bluetooth, Near Field Communication (NFC) or 3G device suitable for communicating with the other medical devices 10 and/or the wireless transceiver 18 of the central server 16.

Figure 3:
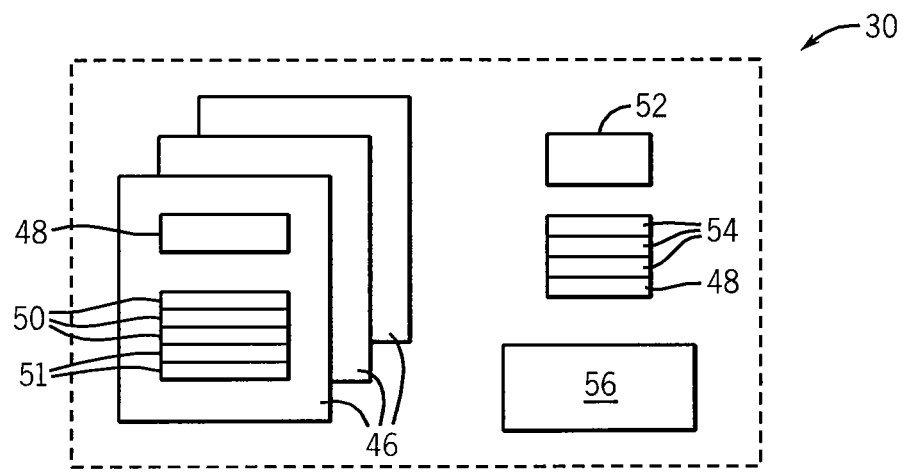
FIG. 3 is a diagram of a data structures held within the memory of the medical device of FIG. 2 according to one embodiment of the invention.

Referring now to FIG. 3, the data structures 30 in the memory 26 (shown in FIG. 2) may include one or more patient data objects 46 each associated with a patient identification number 48 unique to that patient (for example, obtained from a barcode wristband 44) together with static patient-specific predicate data 50 may be entered by the user or obtained through discovery process from a remote device, and real-time patient specific predicate data 51, including for example the status of various sensors on the medical device 10 or other proximate machines 10 as will be described. Normally, only a single patient object 46 is active; however, others may be stored and used if the medical device 10 is used with multiple patients during the day as can occur with portable equipment. The data structure 30 may also include a machine identification code 52 identifying a serial number of the machine and its general class and function, ideally, according to a standard set of identifications used within an industry or by a specific manufacturer.

The data structure 30 may also include task data 54 specific to the particular medical device 10 and its environment and generally describing the operating context of the medical device 10 including, for example, the type of drug being delivered and its programming or data input by medical personnel 38, for example, through data entry keypad 36. In the case of an infusion pump, drug type and infusion rate and volume may be in this task data 54. All or some of the task data 54 may be designated as shareable by flag bits (not shown) that may be programmed at the time of manufacture or entered or modified at a later time. The task data 54 of the data structure 30 may also duplicate the patient identification number 48 reflecting an active patient ID indicating which of the patient objects 46 is active.

Finally the data structure 30 may include machine rules 56 which receive task data 54 to operate the medical device 10 as moderated by context-aware protocols and patient specific predicate data 50 and 51.

Figure 4:
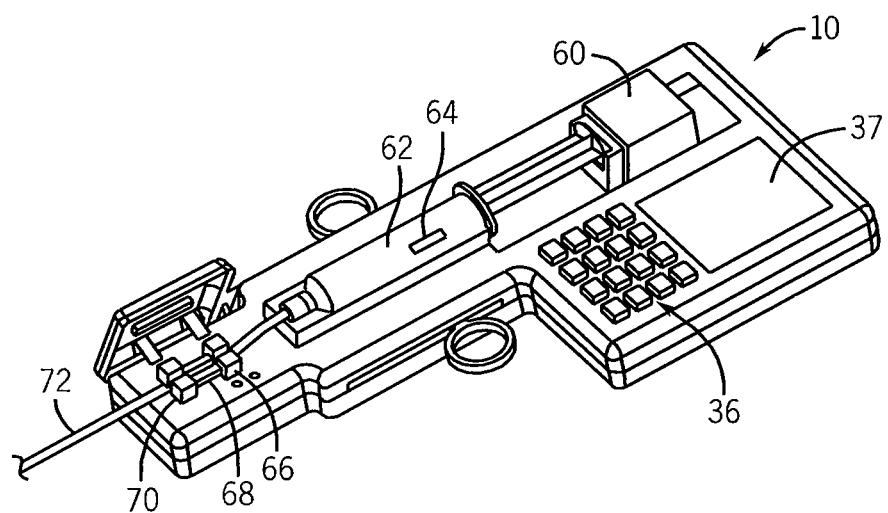
FIG. 4 is a perspective view of example medical device showing automatic drug identification for obtaining task data.

Referring now to FIGS. 2, 3 and 4, in one such medical device 10, for example a syringe pump, the interface 34 may control a syringe plunger mechanism 60 operating to press down the plunger of the syringe 62 containing a particular drug formulation. The syringe 62 may be marked with an RFID tag 64 which may be automatically read by context sensor 42 providing task data 54 indicating the drug formulation in the syringe 62. The task data 54 may also hold information from various sensors on the medical device 10 including an air bubble sensor 66, a pressure sensor 68, and a flow meter 70, which monitor an IV line 72 attached to the syringe 62 and passing to the patient. All of this data provides task data that may be used as input parameters for the machine rules 56 or as real-time predicate data for the protocol, to provide an indication of the intended tasks to be performed by the medical device 10. Syringe pumps suitable for use with the present invention are described in co-pending patent application Ser. No. 13/659,619 filed Oct. 24, 2012 and entitled: "Syringe Pump with Improved Flow Monitoring" hereby incorporated in its entirety by reference.

Figures 5, 6:
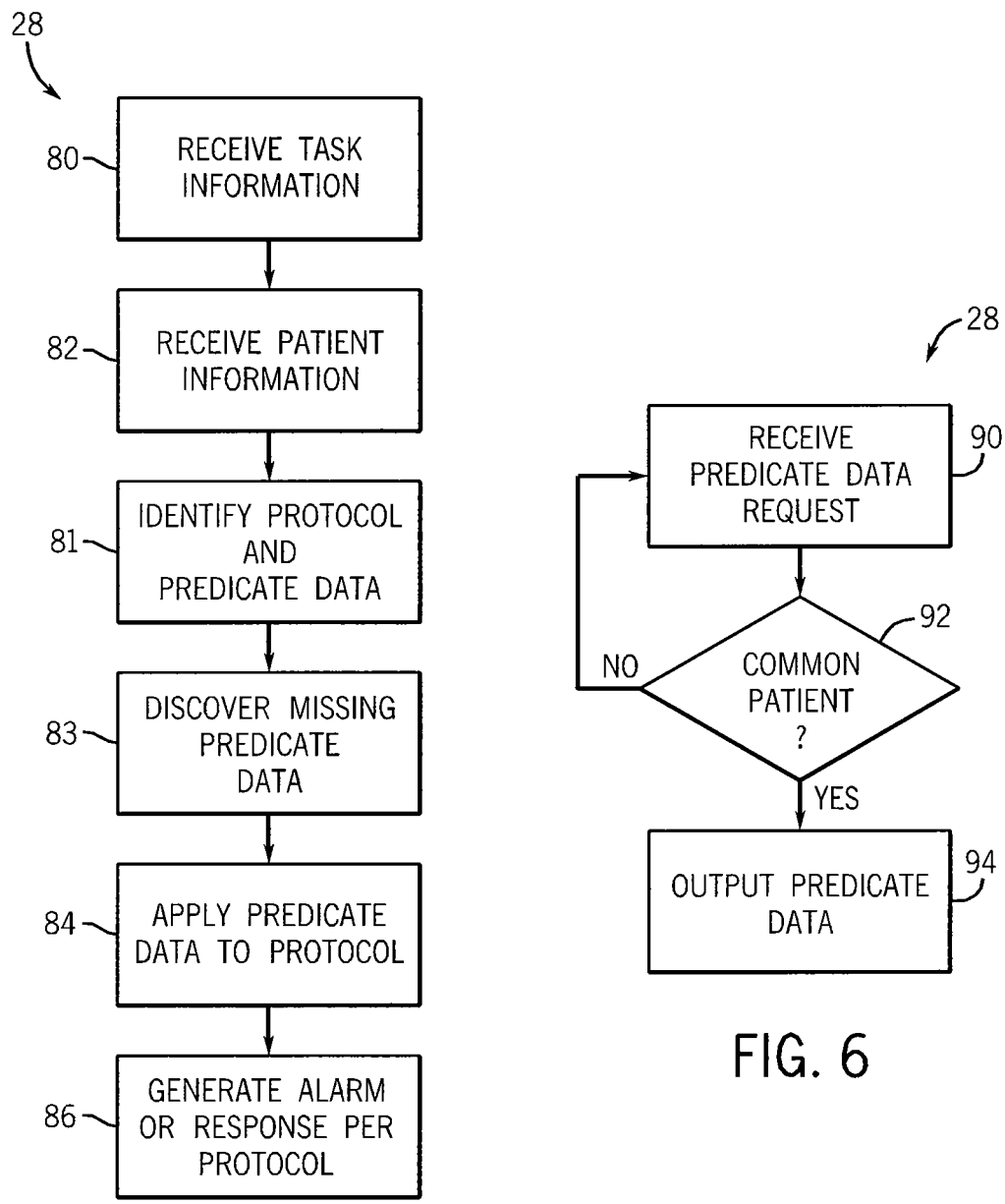
FIG. 5 is a flowchart of the principal steps of operation of the device of FIGS. 2 and 3 in implementing the present invention to provide patient-specific alerts.
FIG. 6 is a flowchart of the steps implemented by the devices of FIGS. 2 and 3 in sharing information with other medical devices.

Referring now to FIGS. 2 and 5, at a first step, as indicated by process block 80, the program 28 may receive task data 54, for example, as entered by hand through data entry keypad 36 or is read from a container of the drug products 37. Generally, for the case of a medical pump, this task data 54 will include the drug type and delivery instructions, for example, a flow rate and/or total volume.

As indicated by process block 82, the program 28 may then receive a patient identification number 48, for example, as keyed through data entry keypad 36 or automatically scanned by barcode reader context sensor 42.

The task data 54 may be used, as indicated by process block 81, to discover context-aware protocol and predicate data governing the steps of the task defined by the task data 54. For example, this protocol data may describe protocols used for a type of drug as a function of particular predicate data including, for example, static predicate data 50 and real-time predicate data 51. Process block 81 may obtain the necessary protocol and predicate data by transmitting data of the task data 54 to a treatment protocol database 15 which uses the identified drug to provide a comprehensive protocol for delivery based on a range of different predicate values. An identification of these predicate values is also obtained in process block 81.

At process block 83, the program 28 evaluates predicate data which currently may not be available in the data structure 30. Static predicate data 50 may be obtained, for example, by communication with the medical database 22 using an index of the patient identification 48. The static information may include the gender and weight and age of the patient and information such as drug allergies.

In this regard, the program 28 may use the patient ID information to obtain the appropriate records and have a priori knowledge of the necessary data fields of the electronic medical record database 22 to obtain information desired for the predicate fields relevant to the particular medical device 10. In one embodiment, the medical device 10 may exploit a universal coding of data of the database 22, for example, as applied by the database server 16 that tags information with common tags, for example XML tags. This predicate data is then enrolled in the data structure 30.

Some non-static predicate data will not be in the medical database 22 and can be collected only dynamically from the patient, for example blood pressure and blood glucose level. For this purpose, the program 28 may prompt the entry of additional data from the medical personnel 38 through the data entry keypad 36. Alternatively, the real-time predicate data 51 may also be obtained from other medical devices also operating on the same patient 12 as indicated by matching active patient ID as will be described below.

The collected context-aware protocol and predicate data may then be applied to the machine rules 56 as indicated by process block 84. Generally these machine rules 56 implement the control loop of the medical device 10 for providing intervention and may make use of information from the sensors and actuators 35 associated with the medical device 10. In one example, the context-aware protocol and predicate data operate to provide input operating parameters to the machine rules 56 which then control the medical device 10 according to those operating parameters. The operating parameters in this context are similar to those that could be implemented through the data entry keypad 36 by a human operator and will control in the case of the medical pump flow rate and the like. Alternatively, the context-aware protocol and predicate data may operate in an advisory capacity to provide alerts and override of the medical device 10 if incorrect operating conditions are chosen or the chosen operating conditions are incorrect given a total context of the patient treatment.

The context-aware protocols, as well as monitoring real-time medical information from the patient may incorporate rules related to the appropriate delivery of drugs according to age and gender and weight and knowledge about drug interactions with respect to other drugs taken by the patient (for example, obtained from the drug fact database 23) to ensure that the drug being delivered by the medical device 10 does not have adverse interactions with other drugs prescribed for the patient as recorded in the electronic medical record database 22. At a top level, the context-aware protocols ensure that the delivered drugs are not contraindicated for the particular medical condition of the patient obtained from the medical database 22. This is in addition to the context-aware protocols operation to provide informed ranges for monitoring the delivery of the drugs based on knowledge of the patient condition obtained from the real-time predicate data 51.

At process block 86 alerts or responses may be automatically generated based on the application of the task data 54 and predicate data 50 and 51 to the machine rules 56 per process block 84. These alerts may be transmitted wirelessly to terminals 20 through the server 16 by the same link that is used to obtain predicate data 50 and 51 or may be local alarms implemented on an annunciator or buzzer or display 39 associated with the particular medical device 10. The responses may include, for example, ceasing of the injection of a drug or other simple actions that can be taken by the medical device 10 absent the presence of medical personnel 38 on a real-time basis. The advisory information can also be made available to patient and caregiver at the care site by medical devices under use, such as showing the message on the medical device screen, or broadcasting audio alert, or playing a video(s) to demonstrate.

Referring now to FIG. 6, as noted above, a given medical device 10 may obtain real-time predicate data from other local medical devices 10 operating on the same patient 12. For example, this predicate data may be that identified in the protocol and predicate is obtained from protocol database 15, or 17. Transfer of predicate information providing a context for the patient treatment may be done by each medical device 10 detecting a request as indicated by process block 90 associated with a patient ID that is active with the requesting device. At decision block 92, the patient ID associated with the request is compared to the patient ID that is currently active with the device receiving the request. If they are the same, then at process block 94 task data 54 that is identified as shareable may be shared over the wireless links with the requesting device according to a matching of the desired predicate data. The shared data may include the machine identification code 52 which provides context for the shareable data or the shareable data may be coded to independently indicate its meaning.

Figure 7:
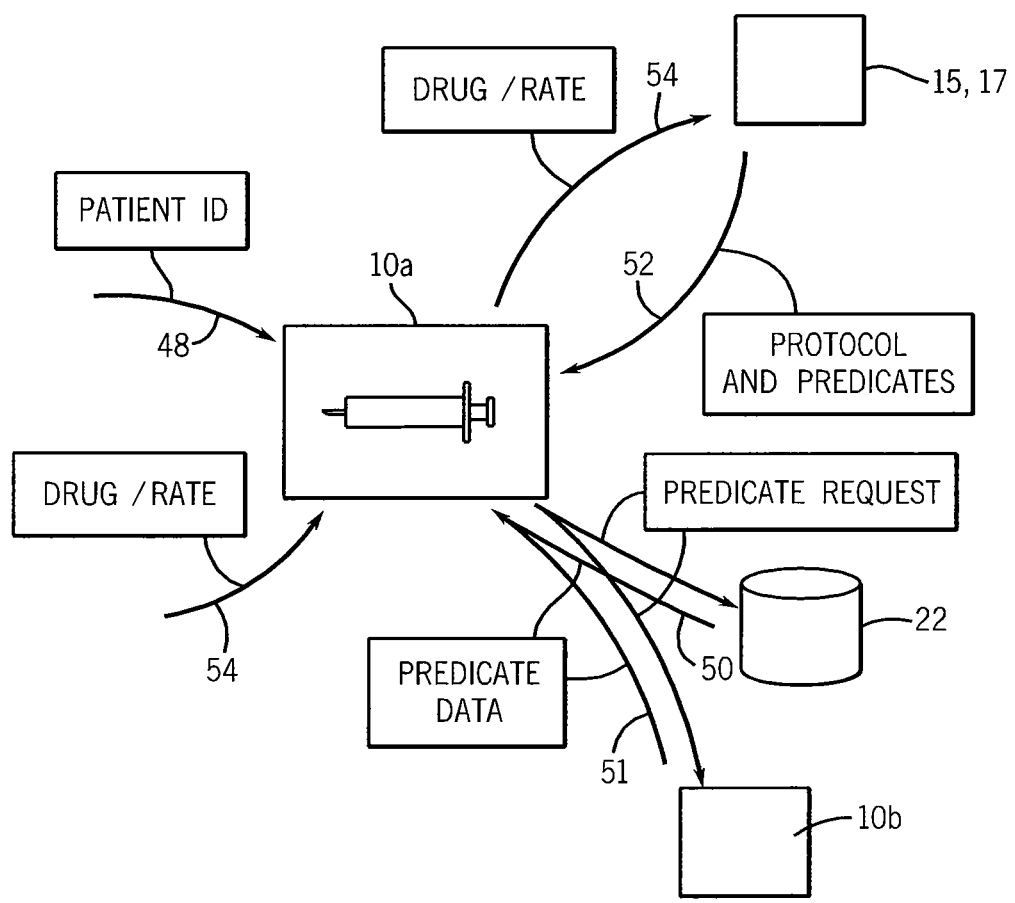
FIG. 7 is a data flow diagram showing the exchange of messages among the medical device and associated medical devices to obtain a contextual understanding.

Referring now to FIG. 7, a given interventional device 10*a* may thus receive basic task data 54 and patient identification number 48, for example, as encoded in a drug container or entered by a user. The task data 54 may be sent by the device 10*a* to a protocol database 15 or 17 to receive context-aware protocol information and an identification of associated predicates 50 and 51. The device 10*a* may make use of the patient identification number 48 and the identification of the predicate data 50 and 51 to obtain necessary predicate data either static predicate data 50 from a medical database 22 or the like or real-time predicate data 51 from other medical devices 10*b*.

Generally the invention relates to medical device systems and methods for inquiring and searching for information, refining searched results, monitoring the status of devices and/or specific task(s), monitoring patient status, storing and processing related data, generating advisory reports and/or alarms, displaying related information and/or authorizing execution of an original or modified treatment plan. The above-mentioned tasks can be performed on a remote site, or on site, in real time, in advance, or post-treatment. While prior art systems have proposed the use of clinically acceptable treatment protocols, such as drug libraries defining clinically accepted dosage (or infusion rate) limits, the presently disclosed systems and methods provide new ways for communication of information, enabling data transferring and processing with 1) multiple devices, including medical and non-medical devices; 2) multiple data sources, including but not limited to drug facts, disease treatment protocols, clinical therapy protocols, patient profiles, lab testing results, etc.; and 3) data obtained at multiple time points, such as patient lab test results history, and/or previous intravenous infusion parameters; enabling generation of a comprehensive advisory report for a specific patient to enhance safety and effectiveness of treatment, mitigation, diagnosis or prevention of a disease or abnormal condition; and enabling an advisory at time of need, including on-site real time advisory.

Instead of conventional "discrete" medical devices, databases, and test results, or traditional "discrete" tasks performed in individual incidences, well communicated and well informed integrated systems are conceptualized to provide more accurate advisory based on real time situations and known trusted knowledge base. Real time clinical decision support at the execution site during treatment, diagnosis, mitigation, prevention, etc, can be provided by such integrated medical devices with awareness of patient context, intent of actions, and clinical protocols.

The present invention relates to systems and methods providing information-based advisory by medical devices, with emphasis on real time advisory at site of care. With rapid expansion of data sources for drug facts, disease treatment protocols, clinical therapy protocols, etc, together with broad applicability of "smart" medical devices with wireless communication and advisory features, better systems and methods of use can be developed to utilize the available knowledge base for a specific patient with specific conditions. The advisory can be provided by a medical device(s) or other related devices. The advisory can be made on a remote site or on site. The timing can be real time, in advance, or post-treatment.

In particular the present invention provides:

(1) patient profile context-awareness;

(2) applied clinical decision support based on remote/onboard knowledge base;

(3) derived clinical diagnosis/treatment intent of the executing medical device through applying patient context to the knowledge base.

(4) clinical intent translates to a suitable range of measurable parameters to be monitored by the medical device.

As the result, the medical device controls/measures a set of parameters with real time awareness of patient current condition. The device measure/controlled parameter domain continue to be adjusted per up-to-date patient profile provided by external content providers. All subsystems act collectively.

One aspect of the present patent application is patient profile context-awareness: enabling the devices to "be aware" of the patient profile and real time conditions, for example, patient gender, age, diagnosis, disease history, lab testing results and historical data, etc. Some or all of the information serves as fundamental data for further inquiry, data processing and/or reporting. By processing information relating to a patient, diagnose/prescription, and/or disease, treatment intent can be extracted from patient profile (age, gender, etc.), symptoms, diagnosis, chart notes, etc, and relevant data source(s). In one embodiment, infusion related information is stored in a database. The inquiry from pump user is transferred by a server to the database, and the result(s) of the inquiry (such as drug infused before, flow rate, patient reaction to the drug, special notes, etc) is transferred back to the pump for the user(s) to review.

One aspect of the present patent application is application of clinical decision support knowledge based on device, remote, and/or onboard knowledge base.

One aspect of the present patent application is constantly applying clinical decision support rules, either onboard a medical device or at a diagnostic/therapeutic procedure administration time with patient context-awareness. Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

What is claimed is:

1. A medical device comprising:
    an interventional element communicating with a patient to perform a medical procedure on the patient;
    a data input device for receiving data related to an interventional task performed by the interventional element;
    a data communication link for electronic data communication with external devices including an external data serving device and at least one external predicate data device; and
    an electronic controller communicating with the interventional element, the data input device, and the data communication link and executing a stored program to:
    (a) transmit the data related to the interventional task to the external data serving device to receive an operation protocol according to the data related to the interventional task, the operation protocol providing rules related to performance of the interventional task and an identification of required predicate data for the performance of the interventional task;
    (b) based on the received operation protocol, discover predicate data of the required predicate data from the at least one external predicate data device; and
    (c) execute and monitor execution of the interventional task according to the received operation protocol and predicate data from the external data serving device and the at least one external predicate data device.

2. The medical device of claim 1 wherein the data communication link is selected from one or more of the group consisting of: a Bluetooth radio link; and infrared data link; a Near Field Communication (NFC); and a Wi-Fi datalink.

3. The medical device of claim 1 wherein the interventional element is a pump for the delivery of a liquid medicament and interventional task is the delivery of liquid medicament.

4. The medical device of claim 3 wherein the data input device is selected from the group consisting of: a keyboard, RFID tag reader, and a barcode scanner.

5. The medical device of claim 3 wherein the pump is selected from the group consisting of a large volume infusion pump, a syringe pump, and an ambulatory pump.

6. The medical device of claim 3 wherein the data communication link is a wireless communication link.

7. The medical device of claim 3 further including an alarm providing an alarm to a user of the medical pump and wherein the electronic controller further executes the stored program to activate the alarm according to the rules of the operation protocol.

8. The medical device of claim 3 wherein the protocol identifies blood pressure as predicate data and a protocol that provides a range of blood pressure during which the pump may operate and causes termination of pump operation when blood pressure moves out of this range and wherein blood pressure is obtained through a separate blood pressure monitor operating as the external monitoring device.

9. The medical device of claim 3 wherein the protocol identifies blood glucose as predicate data and a protocol that provides a range of blood glucose during which the pump may operate and causes termination of pump operation when blood glucose moves out of this range and wherein blood glucose is obtained through a separate blood glucose monitor operating as the external monitoring device.

10. The medical device of claim 3 wherein the data related to interventional task includes drug information identifying the liquid medicament and delivery information identifying at least one of the delivery rate and volume for the liquid medicament.

11. The medical device of claim 10 wherein the data related to the interventional task includes patient identification information.

12. The medical device of claim 11 wherein the external predicate data device is a hospital database providing clinical information about the patient based on the patient identification information.

13. The medical device of claim 11 wherein the external predicate data device is a medical monitoring system proximate to the medical pump providing real-time medical data for the patient based on the patient identification information.

14. The medical device of claim 13 wherein the medical monitoring system is selected from the group consisting of: a blood pressure monitor, a blood oximeter, a glucose monitor; and a respiration monitor.

15. A medical pump delivery system comprising:
a medical sensor system providing:
(a) at least one sensor with a patient to obtain medical information on a real-time basis:
(b) a first data communication link for electronic data communication with external devices including an external data serving device; and
a medical pump system providing:
(a) a pump for the delivery of a liquid medicament;
(b) a data input device for receiving data related to a pump task in delivery of the liquid medicament;
(c) a second data communication link for electronic data communication with external devices including at least one external predicate data device; and
(d) an electronic controller communicating with the pump, the data input device, and the first and second data communication link and executing a stored program to:
(i) transmit the data related to the pump task to the external data serving device to receive an operation protocol according to the data related to the interventional task, the operation protocol providing rules related to performance of the pump task and an identification of required predicate data for the performance of the pump task;
(ii) based on the received operation protocol, discover predicate data of the required predicate data from the at least one external predicate data device; and
(iii) monitor execution of the pump task according to the received operation protocol and predicate data from the external data serving device and the at least one external predicate data device.

16. The medical pump delivery system of claim 15 further including: the external data serving device providing a database linking pump task data to protocols and required predicate data for the protocols.

* * * * *